United States Patent
Barich et al.

(10) Patent No.: US 10,564,098 B2
(45) Date of Patent: Feb. 18, 2020

(54) IMAGE CAPTURE FOR LARGE ANALYTE ARRAYS

(71) Applicant: Bio-Rad Laboratories, Inc., Hercules, CA (US)

(72) Inventors: John Barich, Martinez, CA (US); Renee Lemaire-Adkins, Napa, CA (US); David Neaz, Pleasanton, CA (US); Ariel Notcovich, Walnut Creek, CA (US); Paul Patt, Walnut Creek, CA (US); Ryan Short, Fairfield, CA (US); Steven Swihart, Walnut Creek, CA (US); Evan Thrush, San Anselmo, CA (US); Trey Marlowe, San Francisco, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 1231 days.

(21) Appl. No.: 14/056,162

(22) Filed: Oct. 17, 2013

(65) Prior Publication Data

US 2014/0106989 A1    Apr. 17, 2014

Related U.S. Application Data

(60) Provisional application No. 61/815,456, filed on Apr. 24, 2013, provisional application No. 61/715,103, filed on Oct. 17, 2012.

(51) Int. Cl.
*H04N 5/361*    (2011.01)
*H04N 5/357*    (2011.01)
(Continued)

(52) U.S. Cl.
CPC ......... *G01N 21/63* (2013.01); *G01N 21/6452* (2013.01); *G01N 27/44726* (2013.01);
(Continued)

(58) Field of Classification Search
None
See application file for complete search history.

(56) References Cited

U.S. PATENT DOCUMENTS

| | | | |
|---|---|---|---|
| 4,675,533 | A | 6/1987 | Shimizu |
| 4,788,594 | A | 11/1988 | Ovshinsky et al. |

(Continued)

FOREIGN PATENT DOCUMENTS

| | | | |
|---|---|---|---|
| CN | 102077080 | A | 5/2011 |
| CN | 102375016 | A | 3/2012 |

(Continued)

OTHER PUBLICATIONS

"Gel Documentation System" for Cleaver Scientific; *Science*; 315(5815):1154 (Feb. 2007) author unknown.
(Continued)

*Primary Examiner* — Neil N Turk
(74) *Attorney, Agent, or Firm* — Kilpatrick Townsend and Stockton LLP

(57) ABSTRACT

Analyte arrays such as solutes in a slab-shaped gel following electrophoresis, and particularly arrays that are in excess of 3 cm square and up to 25 cm square and higher, are imaged at distances of 5 cm or less by either forming sub-images of the entire array and stitching together the sub-images by computer-based stitching technology, or by using an array of thin-film photoresponsive elements that is coextensive with the analyte array to form a single image of the array.

18 Claims, 5 Drawing Sheets

(51) Int. Cl.
| | | |
|---|---|---|
| *H04N 5/335* | (2011.01) | |
| *G01N 21/64* | (2006.01) | |
| *G01N 21/63* | (2006.01) | |
| *H04N 5/262* | (2006.01) | |
| *H04N 5/349* | (2011.01) | |
| *G01N 27/447* | (2006.01) | |
| *G02B 21/06* | (2006.01) | |

(52) U.S. Cl.
CPC .......... *H04N 5/2624* (2013.01); *H04N 5/335* (2013.01); *H04N 5/349* (2013.01); *H04N 5/3572* (2013.01); *H04N 5/3575* (2013.01); *H04N 5/361* (2013.01); *G01N 21/6428* (2013.01); *G01N 2021/6484* (2013.01); *G01N 2201/0833* (2013.01); *G01N 2201/10* (2013.01); *G01N 2201/103* (2013.01); *G01N 2201/127* (2013.01); *G02B 21/06* (2013.01)

(56) References Cited

U.S. PATENT DOCUMENTS

| | | | |
|---|---|---|---|
| 4,840,714 A | 6/1989 | Littlehales | |
| 4,853,785 A | 8/1989 | Ovshinsky et al. | |
| 4,889,606 A | 12/1989 | Dyson et al. | |
| 5,013,420 A | 5/1991 | Schuette | |
| 5,356,772 A | 10/1994 | Chan et al. | |
| 5,445,723 A | 8/1995 | Camacho | |
| 5,482,613 A | 1/1996 | Boquet | |
| 5,543,018 A | 8/1996 | Stevens et al. | |
| 5,552,272 A | 9/1996 | Bogart | |
| 5,619,033 A | 4/1997 | Weisfield | |
| 5,710,628 A | 1/1998 | Waterhouse et al. | |
| 5,729,288 A * | 3/1998 | Saito .................. | H04N 5/217 348/243 |
| 5,799,773 A | 9/1998 | Heffelfinger et al. | |
| 5,891,314 A | 4/1999 | Heffelfinger et al. | |
| 5,897,760 A | 4/1999 | Heffelfinger et al. | |
| 5,951,838 A | 9/1999 | Heffelfinger et al. | |
| 6,331,438 B1 | 12/2001 | Aylott et al. | |
| 6,592,734 B2 | 7/2003 | Chen | |
| 7,009,638 B2 | 3/2006 | Gruber et al. | |
| 7,136,094 B2 | 11/2006 | Ziemkowski | |
| 7,265,327 B1 | 9/2007 | Park et al. | |
| 7,499,586 B2 | 3/2009 | Agarwala et al. | |
| 7,499,600 B2 | 3/2009 | Ojanen et al. | |
| 7,532,264 B2 | 5/2009 | Yuan et al. | |
| 7,615,731 B2 | 11/2009 | Heiler et al. | |
| 7,902,004 B2 | 3/2011 | Weisfield et al. | |
| 8,232,531 B2 | 7/2012 | Zentai et al. | |
| 2001/0035559 A1 * | 11/2001 | Ando ................ | G01J 5/02 257/443 |
| 2002/0142306 A1 | 10/2002 | Coleman et al. | |
| 2003/0039383 A1 | 2/2003 | Naghieh et al. | |
| 2003/0068638 A1 | 4/2003 | Cork et al. | |
| 2003/0133009 A1 * | 7/2003 | Brown ................. | G01N 21/253 348/61 |
| 2003/0151735 A1 * | 8/2003 | Blumenfeld ....... | G01N 21/6428 356/73 |
| 2003/0202111 A1 * | 10/2003 | Park .................... | H04N 5/3575 348/243 |
| 2004/0051797 A1 * | 3/2004 | Kelly .................. | H04N 5/361 348/244 |
| 2004/0183928 A1 * | 9/2004 | Tay ...................... | H04N 5/335 348/244 |
| 2004/0233545 A1 | 11/2004 | Jiang | |
| 2005/0064469 A1 * | 3/2005 | Schulz ............ | G01N 33/54366 435/6.11 |
| 2005/0195296 A1 * | 9/2005 | Compton ............ | H04N 5/3651 348/243 |
| 2005/0285952 A1 * | 12/2005 | Kwon .................. | H04N 5/20 348/234 |
| 2006/0051816 A1 * | 3/2006 | Hsieh .................. | G01N 33/58 435/7.9 |
| 2006/0127946 A1 * | 6/2006 | Montagu ............. | G01N 21/6428 435/7.1 |
| 2006/0272946 A1 | 12/2006 | Margalit et al. | |
| 2006/0278531 A1 | 12/2006 | Margalit et al. | |
| 2007/0273775 A1 * | 11/2007 | Jiang .................... | H04N 5/361 348/244 |
| 2007/0279631 A1 | 12/2007 | Yershov | |
| 2008/0081769 A1 * | 4/2008 | Hassibi .................. | C40B 30/04 506/9 |
| 2009/0026079 A1 | 1/2009 | Margalit et al. | |
| 2010/0020933 A1 | 1/2010 | Topfer et al. | |
| 2010/0208872 A1 | 8/2010 | Karellas et al. | |
| 2011/0101243 A1 | 5/2011 | Wimberger-Friedl et al. | |
| 2011/0249910 A1 | 10/2011 | Henderson et al. | |
| 2011/0320174 A1 | 12/2011 | Ragan et al. | |

FOREIGN PATENT DOCUMENTS

| | | |
|---|---|---|
| EP | 0029568 B1 | 6/1981 |
| GB | 2328338 A | 2/1999 |
| JP | 2005-351802 A | 12/2005 |
| WO | 00/62549 A1 | 10/2000 |
| WO | 02/093144 A1 | 11/2002 |
| WO | 2007/110810 A1 | 10/2004 |

OTHER PUBLICATIONS

"Gel documentation UVIDoc-HD2" from Cleaver Scientific. Oct. 2010. 1 page. author unknown.
General Catalog for UVITEC cambridge. "Biomolecular Imaging—Making Light Work"; Jul. 2010 (21 pages) author unknown.
"Odyssey FC Tutorial Manual Version 1.0." Li-Cor Biosciences. Jun. 21, 2010. author unknown.
Schutz-Geschwender et al.; "Quantitative, Two-Color Western Blot Detection With Infrared Fluorescence"; LI-COR Biosciences, published May 2004 (8 pages).
The International Search Report and Written Opinion from PCT/US2013/065377, dated Mar. 13, 2014.
"Nikon CF PlanAPO 4x/0.20 microscope objective lens test", Nov. 28, 2011 (Nov. 28, 2011), XP055302601, Retrieved from the Internet: URL:http://coinimaging.com/nikon_4apo.html [retrieved on Sep. 14, 2016].
David Gilblom, et al., "A real-time, high-resolution camera with an amorphous silicon large-area sensor", Proc. SPIE3302, Digital Solid State Cameras: Designs and Applications, Apr. 1, 1998 (Apr. 1, 1998 ), pp. 29-38, XP55302822, [retrieved on Sep. 15, 2016].
European Search Report dated Sep. 22, 2016 in EP 13846939.0, 11 pages.
First Chinese Office Action dated Aug. 1, 2016; CN Appln. 201380054608.6; 15 pages.
Second Chinese Office Action dated Jun. 2, 2017; CN Appln. 201380054608.6; 8 pages.
Wang, "A Study of CMOS Technologies for Image Sensor Applications", MIT Thesis, Aug. 24, 2001.
Widenhorn et al., "Temperature dependence of dark current in a CCD", Proceedings of SPIE, vol. 4669, 2002.
Chen et al., "A Chip and Pixel Qualification Methodology on Imaging Sensors", NASA Technical Report, 2004.
Kwon et al., "The effects of deuterium annealing on the reduction of dark currents in the CMOS APS", IEEE Transactions on Electron Devices, vol. 51, No. 8, Aug. 2004.
Hijmans et al., "Very High Resolution Interpolated Climate Surfaces for Global Land Areas", International Journal of Climatology, vol. 25, pp. 1965-1978, 2005.
Goiffon et al., "Ionizing Radiation Effects on CMOS Imagers Manufactured in Deep Submicron Process", Proceedings of SPIE, vol. 6816, Mar. 2008.
Dunlap et al., "Dark current in an active pixel complementary metal-oxide-semiconductor sensor", Journal of Electronic Imaging, vol. 20, No. 1, Jan.-Mar. 2011.
European Communication for EP 13846939.0 dated Sep. 19, 2018.

* cited by examiner

IMAGE CAPTURE FOR LARGE ANALYTE ARRAYS

CROSS-REFERENCES TO RELATED APPLICATIONS

The present application claims priority to U.S. Provisional Patent Application No. 61/715,103, entitled "Image Capture for Large Analyte Arrays" and filed Oct. 17, 2012, as well as to U.S. Provisional Patent Application No. 61/815,456, entitled "Image Capture for Large Analyte Arrays" and filed Apr. 24, 2013. Each priority application is herein incorporated by reference in its entirety for all purposes.

BACKGROUND OF THE INVENTION

Many procedures that are performed in biochemical laboratories involve analyses of multiple samples or materials distributed over a two-dimensional area. Examples of such procedures are screening studies performed on substances that are placed in individual wells of a multi-well plate such as a standard 96-well microtiter plate or larger plates, or on molecular species that are applied as droplets or regularly spaced spots, either microscopic in size or larger, on a solid surface. Further examples are slab-shaped electrophoresis gels in which either two-dimensional electrophoretic separations or one-dimensional separations of multiple samples in parallel have been performed. Still further examples are blotting membranes to which electrophoretically separated species in the form of spots or bands have been transferred from a slab gel. Other examples will readily occur to the skilled biochemist. In all of these examples, detections and analyses of the individual sites in the two-dimensional array are often achieved by light energy associated with each site, and may consist simply of determinations of the presence or absence of particular species or may also include quantitative determinations, either on an absolute basis or as comparisons among different sites. The light energy can be transmissive, absorptive, reflective, or generated by the materials at the sites themselves. Species in electrophoresis gels or blotting membranes, for example, are commonly detected by fluorescence, chemiluminescence, or bioluminescence, either as inherent characteristics of the species at the sites or as a result of treatment of the species once they are separated throughout the two-dimensional array. The treatment may include binding reactions in which energy-emitting labels are attached to the species, or irradiation of the species or the labels with excitation energy that will cause them to emit light energy, most often at different wavelengths.

The two-dimensional array, or the planar matrix supporting the array, can be relatively large, for example exceeding about 5 cm, 10 cm, 20 cm, or even 30 cm, in either length, width, or both. In terms of ranges, the length, width, or both, can for example be from about 3 cm to about 100 cm, from about 10 cm to about 75 cm, from about 5 cm to about 50 cm, or from about 5 cm to about 25 cm. In some cases, a large two-dimensional array is divided into a number of narrow strips for independent analysis. In these cases, one may wish to analyze a single strip, two or more but less than all strips, or all strips of the array. When any of these images is taken by a camera, including digital cameras, the arrays are large enough to require placing the camera a considerable distance from the array. One consequence of placing the camera far from the array is that less light is captured. More light can be captured by placing the camera or image acquisition device closer to the array, but this often requires the use of multiple lenses and other optical components to obtain the full image. Some lenses distort the image and geometric resolution can be of limited quality. Intensity roll-off further distorts the image. A type of camera that is commonly used for imaging in biochemical applications is a charge coupled device (CCD) camera, but even with such a camera and its lenses and other optical components, the sensors must be placed well above the object plane, causing the entire apparatus to consume a large amount of space in the laboratory.

SUMMARY OF THE INVENTION

It has now been discovered that analytes that are distributed in a planar array whose lateral dimensions are too large to be imaged without distortion by a camera that is less than approximately 5 cm from the array can indeed be accurately imaged at a distance of 5 cm or less. This can be achieved by forming sub-images of segments of the analyte array and using image stitching technology to combine the sub-images into an image of the entire analyte array. Alternatively, a single image of the entire analyte array can be obtained by use of a thin-film array of photoresponsive elements. The object to be imaged can be the analyte array itself or the planar area in which the analyte array resides and which typically extends beyond the extremities of the analyte array. The planar area can be a planar support matrix for the analyte array, and the matrix can be a multi-well plate, a gel, a blotting membrane, or any surface on which the array has been distributed. When sub-images of segments of the analyte array or supporting planar matrix are used, they can be formed by solid-state image sensors arranged in a two-dimensional array. One or more of the image sensors can be moved or repositioned with respect to the support matrix to acquire multiple sub-images. When a single image is to be formed, this can be achieved by a thin-film array of photoresponsive elements that is coextensive with the analyte array or planar matrix, or larger, combined with thin-film addressing and signal processing circuitry that accesses each of the photoresponsive elements and directs the energy accumulated by each element to an image storage or display device where it is stored or displayed in accordance with the location of each element relative to the array to form the image. A transparent faceplate, such as a fiber optic faceplate or fiber optic taper, can be placed between the image sensors or thin-film array and the analyte array. The transparent faceplate can provide mechanical support to the analyte array and protect the image sensors or thin-film array from damage, such as can occur when the analyte array is wet.

Provided herein is a method of analyzing a plurality of analytes detectable by light emission and arranged in a two-dimensional array. The array is supported by a planar matrix whose length, width, or both length and width measure a minimum of about 3 cm. The method includes placing the planar matrix within 5 cm of a detector. The detector can be either: (1) a plurality of solid-state image sensors that are arranged in a sensor array and that are each positioned to form a sub-image of a segment of the matrix such that the segments collectively cover the entire matrix, and a computer for assembling the sub-images formed at each of the image sensors in accordance with the positions of the image sensors in the sensor array to form an image of the planar matrix in full as a composite of the sub-images; or (2) a plurality of photoresponsive elements arranged in an array that is at least substantially coextensive with the matrix, thin-film addressing circuitry that controls accumulation of energy by, and release of energy from, the photoresponsive elements, and a data storage medium that correlates energy released from the photoresponsive elements with sites on the planar matrix and forms an image of the planar matrix in full from the energy so released.

The method also includes generating the planar matrix image in full by the detector, in a manner that either compensates for or eliminates any irregularities in light intensity across the planar matrix image that are not representative of the two-dimensional array of analytes; and analyzing the analytes from the planar matrix image so generated.

In some embodiments of the method, generating the planar matrix image in full includes applying flat field correction to compensate for or eliminate the irregularities.

In some embodiments of the method, the planar matrix is a slab-shaped gel and the two-dimensional array is generated by electrophoretic separation of the analytes within the gel. In other embodiments, the planar matrix is a blotting membrane and the two-dimensional array is an array of solute bands transferred to the blotting membrane from a slab-shaped gel in which the bands were generated by electrophoretic separation of the analytes within the gel.

In some embodiments of the method, the detector includes a plurality of solid-state image sensors that are arranged in a sensor array and that are each positioned to form a sub-image of a segment of the matrix such that the segments collectively cover the entire matrix, and a computer for assembling the sub-images formed at each of the image sensors in accordance with the positions of the image sensors in the sensor array to form the image of the planar matrix in full as a composite of the sub-images. In one such embodiment, the solid-state image sensors are CCD or CMOS sensors, and the computer includes computer-readable instructions for registering the sub-images, for calibrating the sub-images, and for merging overlapping regions between neighboring sub-images.

In other embodiments of the method, the detector includes a plurality of photoresponsive elements arranged in an array that is at least substantially coextensive with the matrix, thin-film addressing circuitry that controls accumulation of energy by, and release of energy from, the photoresponsive elements, and a data storage medium that correlates energy released from the photoresponsive elements with sites on the planar matrix and forms the image of the planar matrix in full from the energy so released. In one such embodiment, the photoresponsive elements are photodiodes and the thin-firm addressing circuitry includes thin-film field effect transistors.

In some embodiments, the detector defines a planar detection surface, and the method further includes generating a dark signal pattern of each sub-image and subtracting the dark signal pattern from the planar matrix image prior to analyzing the analytes. In some embodiments, the detector defines a planar detection surface, and the method further includes measuring temperature at selected sites along the planar detection surface to determine a temperature pattern, generating a dark signal pattern representative of the temperature pattern, and subtracting the dark signal pattern from the planar matrix image.

In some embodiments of the method, the detector is comprised of pixels and the planar matrix image is generated by passing light from the planar matrix through an array of light pipes to the detector, such that each light pipe directs light to a single pixel.

In some embodiments of the method, a transparent faceplate is placed between the planar matrix and the detector. The transparent faceplate can be, for example, a fiber faceplate or a fiber taper. In some such embodiments, the maximum thickness of the transparent faceplate is about 0.1, 1, 2, 5, 10, 20, or 50 mm.

An additional method is also provided for analyzing a plurality of analytes detectable by light emission and arranged in a two-dimensional analyte array supported by a planar matrix. This method includes: placing the planar matrix within 5 cm of a detector comprising one or more moveable solid-state image sensors; moving the image sensor(s) with respect to the planar matrix and acquiring a plurality of sub-images of the planar matrix; assembling the sub-images into a full image of the planar matrix in accordance with the positions occupied by the image sensor(s) when the sub-images are acquired; and analyzing the analytes using the full image of the planar matrix.

In some embodiments of the additional method, the length, width, or both length and width of the planar matrix measure a minimum of about 3 cm. In some embodiments, assembling includes stitching together at least two of the sub-images. In some embodiments, assembling includes juxtaposing sub-images acquired by the same image sensor.

The additional method can also include the step of compensating for or eliminating any irregularities in light intensity across the full image of the planar matrix, where the irregularities are not representative of the two-dimensional analyte array.

In some embodiments of the additional method, a transparent faceplate is placed between the planar matrix and the detector. The transparent faceplate can be, for example, a fiber faceplate or a fiber taper. The transparent faceplate can provide mechanical support to the analyte array. In some such embodiments, the maximum thickness of the transparent faceplate is about 0.1, 1, 2, 5, 10, 20, or 50 mm.

Details of these and other features of the invention are presented in the sections that follow.

BRIEF DESCRIPTIONS OF THE DRAWINGS

FIG. 1 shows flat field correction and normalization of images according to some embodiments of the invention. Numbers represent faux pixel values. FIG. 1A shows flat field correction of a single image or sub-image of a reference plate. FIG. 1B shows flat field correction and normalization of adjacent sub-images of a reference plate or analyte array. The numbers in bold correspond to pixels that overlap between the two sub-images. Overlap results from the image sensor(s) used to acquire the sub-images being focused on the same area of the reference plate or analyte array. Flat field correction is first applied to each sub-image individually. Then the pixel values for one sub-image are normalized to those of the other sub-image according to the values of the overlapping pixels in the two sub-images.

DESCRIPTION OF SELECTED EMBODIMENTS

Figure 1A:
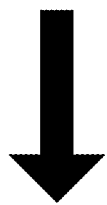

In embodiments involving the use of a plurality of solid-state image sensors forming images of sub-areas of the matrix, such images referred to herein as "sub-images," and stitching together the sub-images in a mosaic to form a full image of the matrix can be achieved by image stitching technologies of the prior art. Examples of image stitching technologies are those that include algorithms for aligning or registering the sub-images by mapping the coordinates of each sub-image to assure that the sub-images are assembled in the correct geometric locations relative to each other, and algorithms for eliminating visible seams by removing or merging overlapping regions between neighboring sub-images. Additional algorithms can also be included in certain embodiments, such as algorithms for calibration of the sub-images and for ghost removal.

Each sensor can contain a two-dimensional array of pixels to produce its sub-image, and the array can be rectilinear. The number of pixels will be great enough to produce an image of the sub-area that shows at least approximate outlines of the shapes of any spots or bands in the area, but in general the number of pixels can vary. In some examples, the number of pixels in the pixel array ranges from about 5×5 (5 rows and 5 columns) to about 1,000×1,000 (1,000 rows and 1,000 columns). An alternate range is from about 10×10 to about 100×100. Each image sensor can be a digital camera whose sensors are either charge-coupled device (CCD) sensors or complementary metal-oxide-semiconductor (CMOS) sensors, or other arrays of photosensitive elements. Beneficial results can be obtained by equipping each digital camera with a lens, selected such that all lenses for all cameras have the same focal length, the focal planes of all cameras are coplanar, and the optical axes of all cameras are parallel to each other.

In some embodiments, the number of sub-images that are stitched together into a full image is equal to the number of image sensors. In these embodiments, the image sensors collectively image an area approximately equal to, or greater than, the area of the entire matrix or analyte array. In other embodiments, by contrast, some image sensors acquire multiple sub-images. These sensors, herein called "moveable sensors", can be repositioned with respect to the matrix, with a new sub-image being acquired at each position, in order for the plurality of image sensors to image the entire matrix.

A moveable sensor can be moved or repositioned as desired. For example, the sensor can be swept in a line or raster-scanned over an area. This can be accomplished by attaching the sensor to a mechanical positioner of the kind used in document scanners or photocopiers. Alternatively, the matrix can be moved while the sensor is held fixed. The portions of the matrix corresponding to the sub-images acquired by one moveable sensor can likewise be arranged in any pattern, such as in a line or grid. In some embodiments, the pixel array contained in a moveable sensor can have equal numbers of rows and columns, as discussed above. In other embodiments, the number of rows and columns in a pixel array can be unequal, with the result that a sub-image is made up of a rectangular or linear array of pixels rather than a square array. If the pixel array is aligned with the direction of movement of the moveable sensor, then having fewer pixels along the direction of movement means that smaller movements are needed to capture consecutive sub-images.

Movement of the sensor with respect to the matrix can occur in discrete steps, with each step corresponding to a distinct sub-image, or can be continuous, with sub-images being acquired at regular time intervals appropriate for the rate of movement. In the latter case, the acquisition time should be short compared with the time interval, so that effectively no movement occurs during acquisition. Stitching of sub-images acquired by a moveable sensor can be performed as discussed above, such as by aligning any overlapping elements in the sub-images, or simply by juxtaposing sub-images resulting from consecutive acquisitions. The latter option reduces the amount of image processing that must be performed to obtain the full image. In some embodiments, the matrix can be imaged using a combination of fixed and moveable image sensors. In other embodiments, only moveable image sensors are used. For example, several image sensors can be arranged in a line, and can be swept over the matrix in concert to obtain a full image of the matrix.

The composite image can be evaluated qualitatively or quantitatively. Quantitative analysis can be used to determine the composition of the sample on which the electrophoresis was performed in terms of the presence or absence of known molecular species in the sample. Such analysis can include correlating each band or spot on the image with a single molecular species or an electrophoretically co-migrating group of species. The correlation can be achieved by comparing the two-dimensional coordinates of the band or spot with those of a standard template in which all positions are identified by their coordinates and by the species that reside at those coordinates. Alternatively, the correlation can be achieved by including standards in the electrophoresis gel in which electrophoretic separation has taken place, alongside or together with the sample or samples to be analyzed. The standards can be mixtures of the same molecular species suspected to be included, or potentially included, in the sample(s), or a series of molecular weight markers spanning the range of molecular weights that are typical among molecular species in samples having the same or a similar origin as the sample(s) being analyzed. The correlation can be performed visually by a laboratory technician, or it can be performed electronically. Visual correlations can be achieved by projecting the composite image onto photographic media or a computer screen. Electronic correlations can be achieved by computer software that collects the information from the pixels and sorts the collected information according to the pixel location, while comparing the information to a library of such information or to standards as described above to identify each spot or band as representing a particular molecular species.

When quantitative analysis is desired, sensors can be used that collect data over a period of time such that each pixel will have an amount of retained data proportional to the intensity of the emission from the site on the matrix that the pixel is focused on. An electronic signal proportional to the accumulated data for each pixel can then be processed and compared to corresponding signals from other pixels to determine relative intensities and thereby the relative amounts of the molecular species. Absolute values can be determined by calibration or by comparison to standards representing known concentrations or amounts of the species. All such signal processing and comparisons can be done by computer, using well-known algorithms, which detect and record the location of each pixel and of the location within the matrix that each pixel represents, and the presence or absence of a signal as well as the signal intensity.

Image generation in the practice of this invention is performed, when necessary, in a manner that eliminates or compensates for any irregularities in light intensity across the planar matrix image that are not attributable to or representative of the analyte array. The expression "across the planar matrix image" is used herein to refer to directions along the surface of the image, i.e., within the plane of the image. These irregularities tend to introduce artifacts, shadings, or light intensity variations in general that do not represent differences among the analytes, and they can arise in various ways. Individual cameras, for example, inherently produce distorted images arising from irregularities among the pixels that form the images. Such distortion is often due to nonuniformities in the optical system, or to the positioning system when moveable sensors are employed, but can arise from other artifacts as well, and in any case interferes with accurate quantitation between the pixels in the array. Compensation for this distortion can be achieved by a calibration technique known in the art as "flat field correction." Examples of flat field correction can be found in Naghieh, H. R., et al., United States Patent Application Publication No. US 2003-0039383 A1 (published Feb. 27, 2003), and in U.S. Pat. No. 5,799,773 (issued Sep. 1, 1998), U.S. Pat. No. 5,891,314 (issued Apr. 6, 1999), U.S. Pat. No. 5,897,760 (issued Apr. 27, 1999), and U.S. Pat. No. 5,951,838 (issued Sep. 14, 1999) (all listing Heffelfinger, D. M., and C. Van Horn as inventors). The methods described in the Heffelfinger and Van Horn patents variously include calibrations of the lens and detector assemblies, use of a scanning light source to achieve uniform illumination, use of a mirror or beamsplitter to sample the source, or the generation of correction data over a range of aperture and magnification settings. The method described in the Naghieh et al. publication involves comparing the image of the array of interest to the image of a reference plate that responds to incident light uniformly along its length and width. Thus, for example, the reference plate is uniformly absorptive and/or transmissive of light, or contains fluorescent material uniformly distributed throughout the plate and is uniformly excitable by incident light. The reference plate is placed in the imaging system independently of, and in place of, the array sought to be imaged, and an image of the reference plate is taken in the same manner as the image of the array. The two images are then compared on a pixel-by-pixel basis, and the gel image is corrected by an appropriate formula or algorithm that accounts for any non-uniformities or deviations in the reference plate image. The image of the reference plate is termed a flat field image, and the corrected image of the gel is termed a flat field-corrected image.

The flat-field correction technique of Naghieh et al. will be described in more detail, with the understanding however that this is but one example of such a technique.

In accordance with the Naghieh et al. technique, the reference plate can be a flat plate having the same dimensions as the array sought to be imaged or, when only a portion of the array is of interest the dimensions of the reference plate will be at least as great as those of the portion. The plate can be from one-sixteenth inch (0.16 cm) to one-half inch (1.27 cm) in thickness, or as an example, approximately one-eighth inch (0.32 cm) in thickness. The plate will be one that responds to incident light uniformly along its length and width, i.e., it contains no nonuniformities that would cause it to either absorb or transmit light differently at any point on the plate than at any other point. When the plate is a fluorescent plate, it will be one that transmits light without transmitting an image of the light source and will either be colored with a fluorescent dye or white. The plate will be constructed to disperse the light striking it from the light source and to emit the light toward the detector in a manner that includes no spatial variations other than those attributable to the light source. For arrays that contain fluorescent labels, a particularly useful reference plate is one that has a fluorescent dye, such as a red or orange dye. For arrays that involve absorption of light from the light source rather than emission, a translucent fluorescent white reference plate that converts ultraviolet light from the light source to white light is particularly useful.

The image of the analyte array can be taken either before or after the image of the reference plate. In either case, the image of the reference plate can be stored as digital data for use in correcting the image of the analyte array. Correction can be achieved by any formula or algorithm that compares the two images and corrects the analyte array image on the basis of nonuniformities or deviations in the reference image (FIG. 1A). This comparison and correction are readily performed by software, which can then display the corrected image. When the images consist of two-dimensional arrays of pixels whose locations in the array are defined by orthogonal coordinates X and Y, one example of correction formula is as follows:

$$Piff(XY) = Pi(XY) \times \left( \frac{Av_{Flat}}{P(XY)_{Flat}} \right)$$

in which:
  Piff(XY) is the corrected value of the pixel at position XY
  Pi(XY) is the value of the pixel at position XY before correction
  $Av_{flat}$ is a coefficient obtained from the average of the values obtained with the reference plate, and
  $P(XY)_{Flat}$ is the value of the pixel at position XY of the reference plate.

Other algorithms and methods of correction will be readily apparent to those skilled in the art. Once the correction has been made, the corrected pixels can be reassembled to form the corrected image.

Figure 1B:
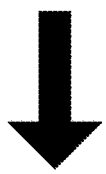
Figure 1B:
Figure 1B:
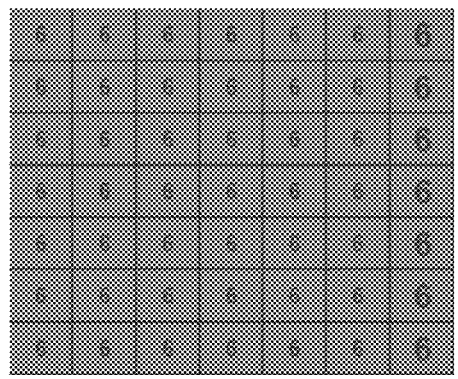
Figure 1B:
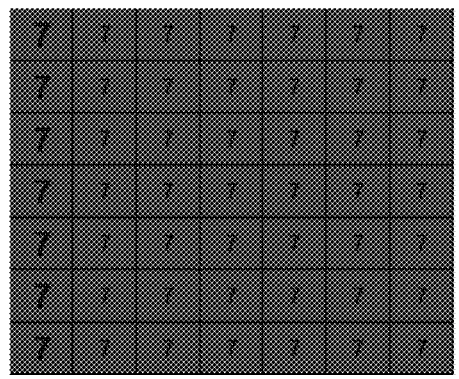
Figure 1B:
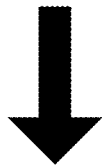
Figure 1B:
Figure 1B:
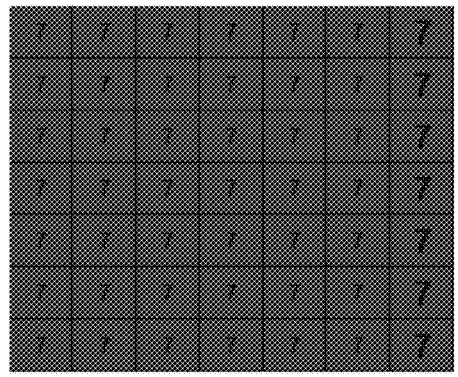
Figure 1B:
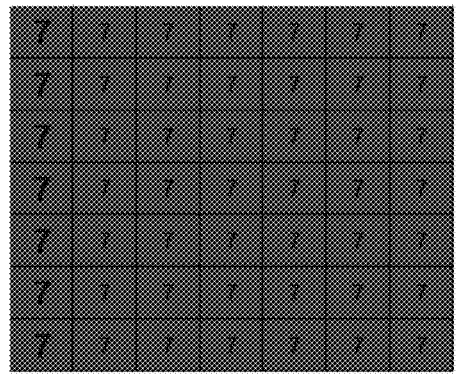

In embodiments of the invention in which imaging of the analyte array is achieved by first forming sub-images or segments of the analyte array with individual image sensors or cameras, flat field correction can be performed on the composite image to compensate for differences in response between the various cameras, or differences for the same camera arising over time or at various locations. Using adjacent sub-images as an example, this type of correction can be achieved by focusing facing edges of the two sub-images on the same line of pixels, thereby causing the two sub-images to overlap at these pixels. A comparison between the intensities of these pixels in one sub-image with those of the other sub-image will provide a correction factor, which can then be applied to all pixels of one sub-image, thereby normalizing the two sub-images (FIG. 1B). Flat field correction can thus be used both within each sub-image and between different sub-images.

Descriptions of the formation of sub-images and the stitching together of sub-images to achieve a composite image are found in Shimizu (Canon Kabushiki Kaisha) U.S. Pat. No. 4,675,533 (Jun. 23, 1987), Gruber et al. (Vexcel Imaging GmbH) U.S. Pat. No. 7,009,638 B2 (Mar. 7, 2006), Ziemkowski (Hewlett-Packard Development Company) U.S. Pat. No. 7,136,094 (Nov. 14, 2006), Agarwala et al. (Microsoft Corporation) U.S. Pat. No. 7,499,586 B2 (Mar. 3, 2009), Ojanen et al. (Nokia Corporation) U.S. Pat. No. 7,499,600 B2 (Mar. 3, 2009), and Regents of the University of Minnesota International Patent Application Publication No. WO 02/093144 A1 (Nov. 21, 2002).

In embodiments of the invention that utilize an array of photoresponsive elements, the lateral dimensions of the array are the same size as the matrix or larger, i.e., the array is at least coextensive with the matrix, and a single image of the entire matrix that is at least approximately the same size as the matrix is formed on the array. The number of photoresponsive elements in the array can vary widely, but will most often be at least 1,000×1,000, and in many cases within the range of 1,000×1,000 to 1,000,000×1,000,000, or even a range of 1,000×1,000 to 10,000,000×10,000,000. The photoresponsive elements receive light energy from the sites on the matrix with which the elements are aligned, and the elements generate detectable electrical signals that are representative of the energy that they receive from the matrix. The electrical signals are stored in a data storage medium from which they can be projected or otherwise made visible or detectable as an image of the matrix.

Any of a variety of known photoresponsive elements can be used, examples of which are photodiodes, phototransistors, photoresistors, and photovoltaic devices. The photoresponsive elements include at least one layer of semiconductor material, preferably silicon semiconductor alloy material, examples of which are amorphous silicon alloy materials, amorphous germanium alloy materials, amorphous silicon carbon alloy materials, and amorphous silicon germanium alloy materials. When photodiodes are used, each one can include two oppositely doped layers of the semiconductor material, optionally with a layer of intrinsic semiconductor material interposed between them, thereby forming a p-i-n type photodiode. In certain embodiments, the array further includes an addressing mechanism for independently accessing each photoresponsive element. An example of such a mechanism is one that includes electrically conductive lines arranged in an x-y matrix and a blocking element associated with each photoresponsive element, such as a diode, a transistor, a resistor, a threshold switch, or a relay. The addressing circuitry can either be separate from the sensor array or integrated with the sensor array on a common substrate.

Photosensors and their associated components for this type of array are known in the art. Examples are certain sensors developed for x-ray imaging, particularly those made for large areas and that involve low read noise and low dark current noise. Two technologies for x-ray imaging that utilize sensors of this type are thin-film field effect transistor (TFT) technology and CMOS. The pixel elements used in the arrays in these technologies are generally large (50-200 µm), a feature that makes these arrays particularly useful in the practice of the present invention. Thus, in certain embodiments, x-ray imaging techniques are used for gel documentation and chemiluminescence imaging.

Architectures vary widely among different photosensors, and a general understanding of the fundamental structure and function of photosensors for use in this invention can be obtained by consideration of one illustrative class of photosensors, i.e., that of a combination of a photodiode and a TFT. The architectures and fabrication methods of TFTs vary widely as well, but according to one example, a 1200 Å layer of titanium-tungsten (TiW), chromium, molybdenum, or tantalum, is first formed over an 800 Å layer of aluminum on a substrate to serve as a metal gate electrode. A 3000 Å gate dielectric layer of silicon nitride ($SiN_x$) is then formed over the metal gate electrode, and a 300-500 Å layer of hydrogenated amorphous silicon (a-Si:H) is formed over the gate dielectric layer. A 1500 Å etch stopper layer of $SiN_x$ is formed over the a-Si:H layer above the gate electrode, and a 500-1000 Å n+ layer is formed over the a-Si:H layer and partially over the etch stopper layer. A 500 Å TiW layer is formed over the n+ layer and a 0.5µ Al layer is formed over the TiW layer to serve as a barrier preventing the Al layer from interacting with the n+ layer. The n+ layer, the TiW metal layer, and the Al layer on the left side of the etch stopper serve as the source electrode of the TFT, and the n+ layer, the TiW metal layer and the Al layer on the right side of the etch stopper serve as the drain electrode of the TFT. A 0.5-2.0µ silicon oxynitride (SiON) layer with a via hole is formed over the TFT, and a 500-1000 Å n+ doped layer is formed over the SiON layer, making contact with the drain electrode. An undoped 0.5-2.0µ a-Si:H layer is formed over the n+ doped layer, a 100 Å p+ doped layer is formed over the undoped a-Si:H layer, and a 500-1000 Å indium-tin-oxide (ITO) transparent conductive layer is formed over the p+ doped layer. A 0.5-2.0µ silicon oxynitride (SiON) layer with a via hole is formed over the conductive layer, and a bias contact, which is a 500 Å layer of TiW beneath a 0.5-1.0µ layer of Al, is formed over the SiON layer, contacting the conductive layer. Finally, a 0.5-1.0µ passivation layer of SiON is formed over both the conductive layer and the bias contact. Adjacent photodiodes are separated by a notch passing through the n+ doped layer, the a-Si:H layer, the p+ doped layer.

The photodiode can be formed over the TFT in a variety of ways. According to one example, a SiON layer is formed over the TFT, then masked and etched to form a via hole exposing the drain electrode. An n+ doped layer is then formed over the SiON layer making contact with the drain electrode. An a-Si:H layer is then formed over the n+ doped layer, a p+ doped layer is formed over the a-Si:H layer, and a conductive layer is formed over the p+ doped layer. The conductive layer is masked and etched to form a notch that exposes the SiON layer. A SiON layer is then formed over the conductive layer and fills the notch, thereby preventing the metal bias layer from shorting out the photodiode and from providing a connection across the etch through the n+ layer. The SiON layer is then masked and etched to form a via hole, and a metal bias layer is formed over the SiON layer to contact the conductive layer through the via hole. The metal bias layer is then masked and etched to form a bias contact. A passivation layer is then formed over both the conductive layer and the bias contact to complete the photodiode. The filled notches thus isolate the photodiodes from each other so that they can accumulate charges independently. Each photodiode is biased by applying a voltage on the bias contact which induces an electric field in the a-Si:H layer. When light enters the a-Si:H layer, electron-hole pairs are generated and are swept by the electric field to opposite sides of the photodiode where they accumulate near the conductive layer and the n+ doped layer. During operation, the TFTs are turned OFF to allow the photodiodes to accumulate charge based on incident light. Upon receipt of a control signal from an external controller, a TFT turns ON and, the accumulated charge is allowed to flow as current through source electrode to components that amplify and process the received image signal.

The electrical signals generated by the photosensor array can be conveyed to a conventional image storage or display device. Examples are magnetic, optical, semiconductor and bubble memory devices. A video display terminal, a photographic film, or a phase change optical data storage medium can be used. The camera that contains the photosensor array can contain a trigger mechanism for initiating the reading of the information that is released by the TFTs and a mechanism for writing the information thus read onto the storage medium. The resulting image can be analyzed visually on a qualitative or quantitative basis, either by a laboratory technician or by instrumentation.

Within each image or sub-image, an amount of dark signal of a magnitude that is great enough to impair or limit the sensitivity of the sensor can occur. "Dark signal" is defined as the response of a photosensitive element in the absence of light. One source of sensor limitation from dark signal is fundamental shot noise. Another is fixed pattern noise. For large area sensors, noise from dark signal can become very large due to the large size of the sensor array. Physical processes that produce dark signal usually increase with increasing amounts of material used in the photosensitive element. The sensitivity of the photosensor array can be increased significantly by removing fixed pattern dark noise. This can be achieved by producing a dark signal pattern for the sensor array and subtracting the dark signal pattern from the measurement pattern generated by the array. The dark signal pattern can vary with temperature, time, or both, and can thus be characterized as a function of these two variables. For example, a temperature measurement can be made and the dark current pattern can be adjusted accordingly to subtract the fixed pattern dark current. The temperature can also vary between different photosensors within the photosensor array. To compensate for this, a plurality of temperature measurements can be taken at different locations within the photosensor array, i.e., at selected sites along the planar detection surface formed by the array, to determine temperature variations along the surface and the resulting temperature pattern. The dark signal pattern can then be adjusted accordingly.

Image sensors at times experience anomalous events that cause individual pixels or groups of pixels to register an abnormal responses when compared to adjacent pixels, responses that are not representative of the sample. Such events are caused, for example, by external electromagnetic radiation or impacts of high energy particles from space or radioactive material, in addition to the dark signal cited above, while the origins of certain of the responses are not understood. The frequency of these anomalous events increases with increasing area of the photosensor array. The responses of the pixels to these events can be corrected by various signal processing techniques. For example, one can determine whether a particular pixel is undergoing an anomalous response by comparing the response at that pixel to those of neighboring pixels. If the response at the pixel is deemed not to be representative of the measurement and thereby anomalous, the response at that pixel can be corrected or removed.

Photosensor arrays often contain manufacturing defects or dark signal defects introduced at the photosensor manufacturing stage, and such defects can have impacts on individual pixels, rows of pixels, columns of pixels, or other sections of the sensor array. The number of defects tends to increase with increasing size of the photosensor array. Correction of these defects can improve both sensitivity and the qualitative appearance of image, as well as manufacturing yields, and such correction can be achieved by hardware, software, or both. For example, if an entire column of a photosensor array fails to function properly, that column can be replaced by simply averaging adjacent columns on either side.

Since the sample to be imaged (i.e., the analyte array) is placed in proximity to the photosensor array, one may wish to protect the photosensor array from the sample, particularly with wet samples and/or samples with which physical contact is to be avoided. Protection can be achieved by depositing or bonding a thin layer of material directly on or to the sensor surface to serve as a faceplate. The material must be transparent to the light being detected. A thin glass element with a thickness approximately equal to or less than less than the size of a pixel on the photosensor can be used as a faceplate, to avoid significant spreading of the light as it passes from the sample to the detector surface. For example, a glass layer 100 micron in thickness can be used, and the sample can be placed directly onto the glass layer and analyzed without significant loss in spatial resolution. Any light spreading and consequent loss in spatial resolution introduced by the protective layer can be corrected by appropriate software algorithms.

Another means of improving the sensitivity of the photosensor array is to place a layer of material over the array that guides the light to each sensor and thereby reduces or eliminates lateral diffusion to adjacent sensors to improve spatial resolution. An example of such a material is one that contains light pipes arranged in a pixelated pattern, i.e., each pixel receiving light through a separate light pipe, or a separate group of light pipes. This can be achieved with a fiber optic faceplate (also called a fiber faceplate), which is a coherent bundle of short optical fibers.

Figure 2:
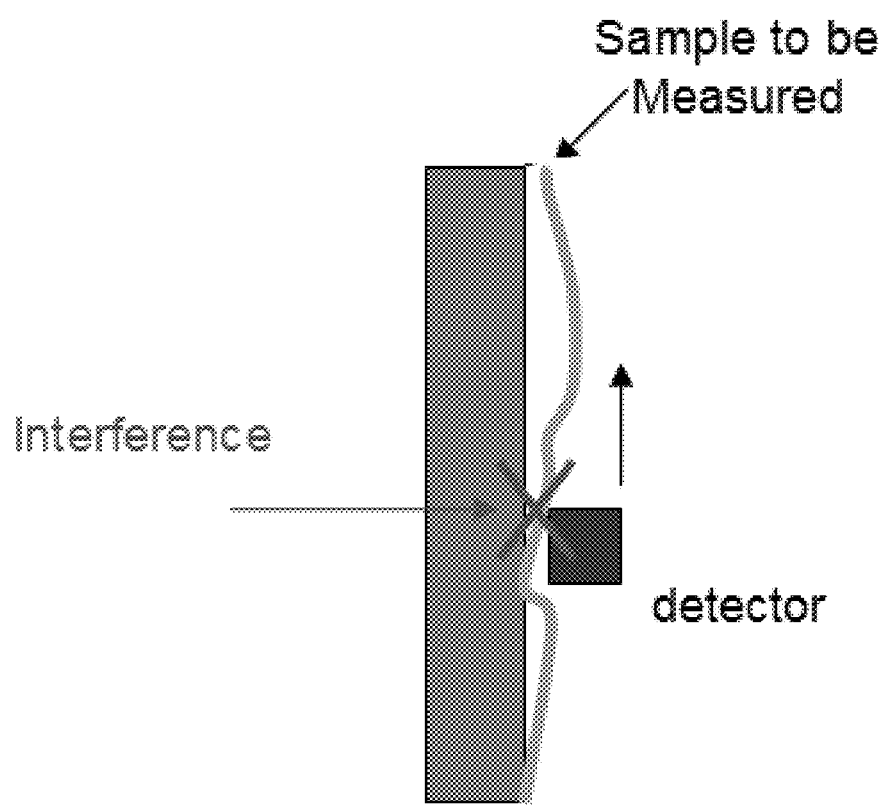
FIG. 2 shows mechanical interference or contact between an image sensor and a sample during scanning of the sensor over the sample. Such interference is undesirable and can be avoided in some embodiments of the methods and apparatus presented herein.
Figure 3:
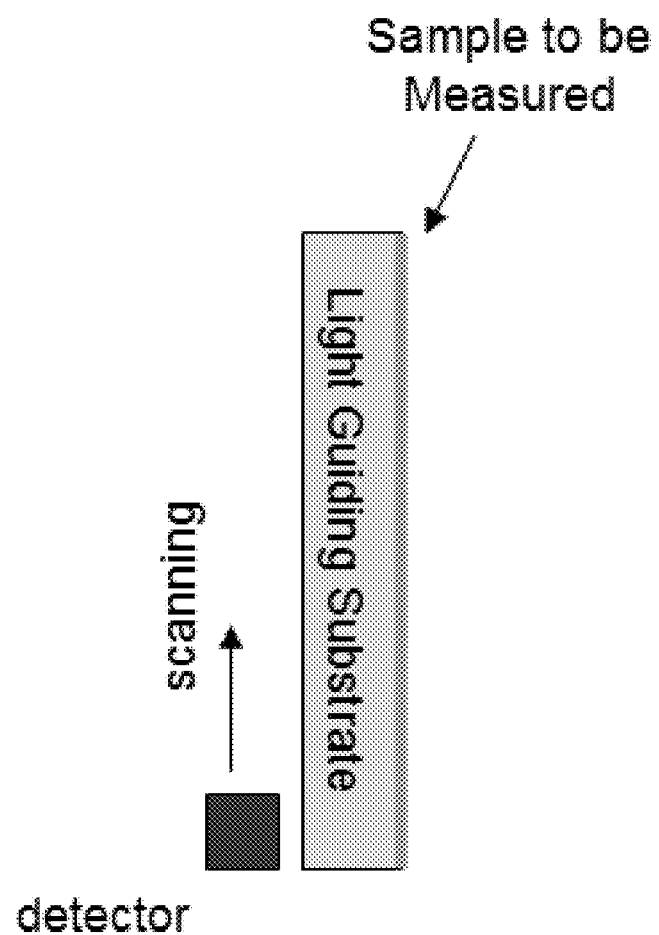
FIG. 3 shows scanning of a solid-state image sensor over a sample (e.g., an analyte array) with a layer of light-guiding material (e.g., a fiber faceplate) placed between the sensor and sample.

A transparent faceplate, for example a thin layer of glass or plastic or a fiber faceplate, can also be used in embodiments of the invention where the sample is imaged using a plurality of solid-state image sensors, and in particular where one or more sensors is scanned over the sample, as discussed above. Here, the faceplate can be placed between the sample and the sensors, and can provide mechanical support to the sample. The faceplate also provides a flat surface that prevents contact between a sensor and the sample, which may occur if the sensor is scanned directly over the sample or if the sample is irregularly shaped (for example, due to being wet) (see FIGS. 2 and 3). Thus, the faceplate prevents damage to the sensor resulting from such contact, while the sample and sensor(s) remain close together. In embodiments where the transparent faceplate provides mechanical support to the sample and protects the sensor, the transparent faceplate is preferably a fiber faceplate or made of a light-guiding material. This allows the faceplate to be thick enough to provide support without causing a loss of resolution or sensitivity. A thick faceplate can be used when one or more sensors are scanned over the sample, or in other embodiments where the sensors do not support the sample. By contrast, when the sample is detected using a thin-film array, a thinner faceplate can be used because the array mechanically supports the sample.

In embodiments of the invention using glass faceplates, a tradeoff is involved between supporting the sample and protecting the sensor on one hand, and allowing the high-resolution transmission of light between them on the other hand. This is because, in this context, glass and other non-light-guiding materials offer greater strength but poorer resolution as the thickness of the faceplate is increased. In embodiments using fiber faceplates, however, the faceplate can be made thick enough (e.g. 1-30 mm) to provide robust mechanical strength while also allowing transmission of light with very little loss or spreading. The fiber faceplate can be positioned so that the optical fibers making up the faceplate are oriented parallel to the direction of light transmission. Fiber faceplates suitable for these embodiments are available from InCom (part no. B7D61-6) and Edmund Optics (part no. 55-142), among others. In general, the maximum thickness of the transparent faceplate can be about 0.1, 1, 2, 5, 10, 20, or 50 mm.

Figure 4:
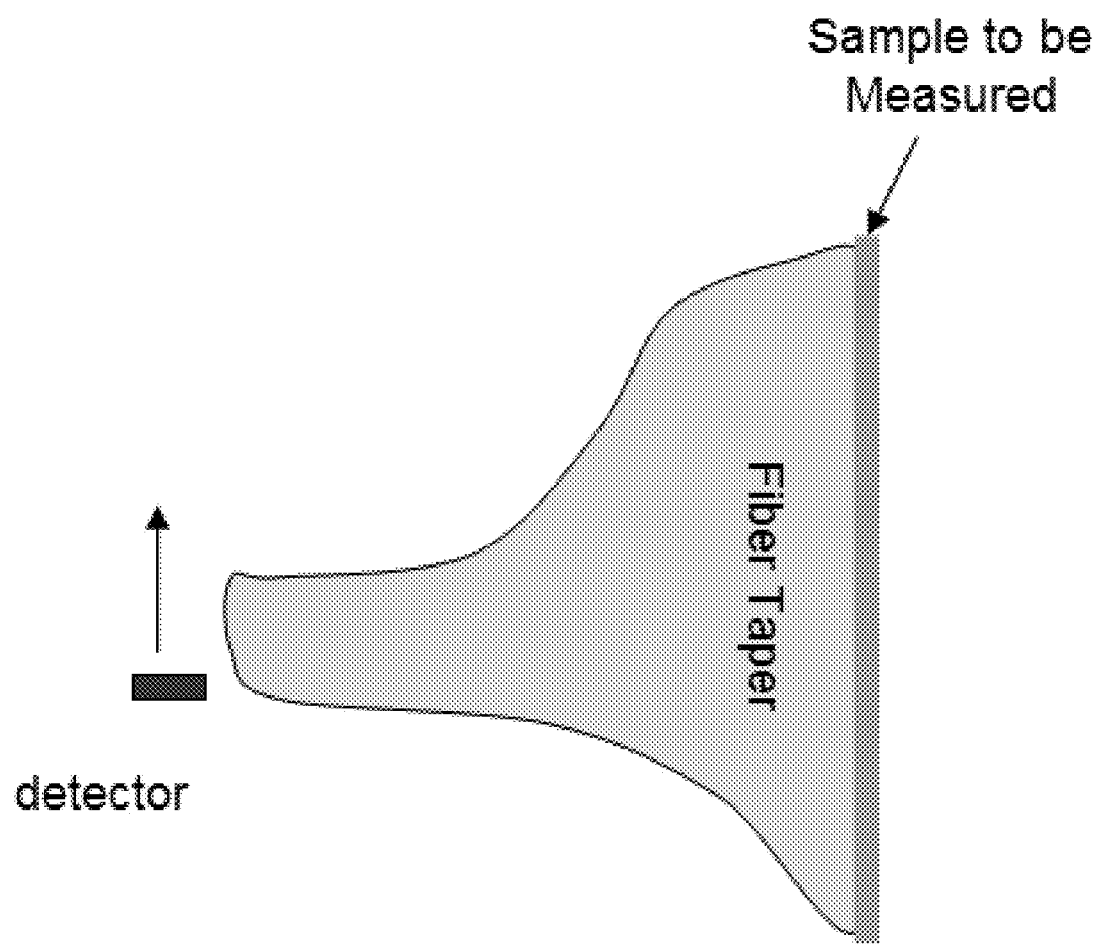
FIG. 4 shows scanning of a solid-state image sensor over a sample (e.g., an analyte array) with a fiber optic taper placed between the sensor and sample.

Fiber optic tapers (e.g. Edmund Optics part no. 55-139) are another kind of faceplate that can be used to separate the sample from solid-state image sensors or a thin-film array. Like a fiber faceplate, a fiber optic taper (also called a fiber taper or simply a taper) comprises a bundle of coherent optical fibers, but the fibers have larger diameters at one end than at the other end. As a result, the two functional surfaces of the taper have unequal areas, with the surface corresponding to the thicker ends of the fibers having greater area. In embodiments where solid-state image sensors are used, a sensor may be placed adjacent to the small surface of a fiber taper, so that the image of the sample (or a portion thereof) passing through the taper is magnified. A fixed individual sensor can thus acquire a sub-image corresponding to a larger area of the sample, without placing the sensor farther from the sample or losing resolution. Alternatively, a moveable sensor can be scanned over the small surface of the fiber taper, requiring smaller (or fewer) movements than would be necessary to image the same portion of the sample in the absence of the fiber taper (FIG. 4). In embodiments employing a thin film-array, the array can likewise be placed adjacent to the smaller surface of the fiber taper. This allows a thin-film array smaller than the sample to capture an image of the entire sample. It is also possible to move a thin film array and a fiber taper in a coordinated fashion with respect to sample, such as by scanning over the sample, to permit imaging of very large samples.

In embodiments employing a thin-film array, certain sources of noise associated with dark signal discussed above can be mitigated by cooling the photosensor array, since dark signal occurrence is often reduced when the sensor temperature is reduced. Cooling of the photosensor array may result in undesired cooling of the sample (the analyte array), however. In chemiluminescence applications, for example, cooling the sample may reduce the intensity of the light produced by the sample. Sample cooling can be mitigated by thermally isolating the photosensor array from the sample by placing a thermally insulating material between the sample and the array. Alternatively, the adverse effects of sample cooling can be avoided by timing of the measurement, i.e., by cooling the sensor array before the sample is brought in close contact with the array, then drawing the sample toward the array and conducting the measurement quickly before the sample has time to cool. The same result may be achieved by heating the sample with an indium tin oxide (ITO) layer or by infrared radiation while cooling the sensor.

Descriptions of thin film arrays of the types described above and their use are found in Ovshinsky et al. (Energy Conversion Devices, Inc.) U.S. Pat. No. 4,788,594 (Nov. 29, 1988), Ovshinsky et al. (Energy Conversion Devices, Inc.) U.S. Pat. No. 4,853,785 (Aug. 1, 1989), Weisfield (Xerox Corporation) U.S. Pat. No. 5,619,033 (Apr. 8, 1997), Park et al. (dpiX, L.L.C.) U.S. Pat. No. 7,265,327 B1 (Sep. 4, 2007), Yuan et al. (DPIX LLC) U.S. Pat. No. 7,532,264 (May 12, 2009), Weisfield et al. (Xerox Corporation) U.S. Pat. No. 7,902,004 (Mar. 8, 2011), and Zentai et al. (Varian Medical Systems, Inc. and dpiX, L.L.C.) U.S. Pat. No. 8,232,531, B2 (Jul. 31, 2012).

The planar matrix that serves as a support for the array of molecular species can be either a slab gel in which electrophoresis has been performed to achieve the separation, a blotting membrane to which the bands or spots in a gel have been transferred, or any of a variety of other spatial arrays or patterns that are obtained in a variety of ways and are used for a variety of purposes. Proteins, nucleic acids, or other biological species that have been electrophoretically separated in a slab gel are often transferred to a blotting membrane formed of nitrocellulose, nylon, polyvinyl difluoride, or similar materials prior to identification and quantification. A common transfer technique is electroblotting, in which flat surfaces of the gel and membrane are placed in direct contact and an electric current is passed through both the gel and the membrane in a transverse direction, thereby transferring the species in a manner similar to that by which the species were mobilized within the gel. When the species are DNA fragments, the transfer is termed a Southern blot after its originator, the British biologist Edwin M. Southern. By analogy, the transfer of RNA fragments is termed northern blotting, and the transfer of proteins or polypeptides is termed western blotting. Still further examples are "eastern" blots for post-translational modifications, and "far western" blots for protein interactions.

Electroblotting can be performed in either a wet, dry, or semi-dry format. In wet blotting, the gel and membrane are layered over each other in a stack which is immersed in a transfer buffer solution in a tank on whose walls are mounted wire or plate electrodes. The electrodes are then energized to cause the solutes to migrate from the gel to the membrane. In semi-dry blotting, filter papers wetted with the transfer buffer solution are placed on the top and bottom of the stack with the gel and the membrane in between to form a "blotting sandwich." The electrodes are then placed in direct contact with the exposed surfaces of the wetted filter papers. In dry electroblotting, no liquid buffers are used other than those residing in the gels. Descriptions of wet, dry, and semi-dry electroblotting and the associated materials and equipment are found in Margalit et al. (Invitrogen) United States Patent Application Publications No. US 2006/0272946 A1 (Dec. 7, 2006), No. US 2006/0278531 A1 (Dec. 14, 2006), and No. US 2009/0026079 A1 (Jan. 29, 2009); Littlehales (American Bionetics) U.S. Pat. No. 4,840,714 (Jun. 20, 1989); Dyson et al. (Amersham International) U.S. Pat. No. 4,889,606 (Dec. 26, 1989); Schuette (Life Technologies, Inc.), U.S. Pat. No. 5,013,420 (May 7, 1991); Chan et al. (Abbott Laboratories), U.S. Pat. No. 5,356,772 (Oct. 18, 1994); Camacho (Hoefer Scientific Instruments), U.S. Pat. No. 5,445,723 (Aug. 29, 2005); Boquet (Bertin & Cie), U.S. Pat. No. 5,482,613 (Jan. 9, 1996); and Chen (Wealtec Enterprise Co., Ltd.) U.S. Pat. No. 6,592,734 (Jul. 15, 2003).

Regardless of the electroblotting format, the resulting electroblot is often treated with detection reagents to render the bands or spots in the blot detectable to the photosensors or photoresponsive elements in the detector array by methods appropriate to the species in the bands or spots. In Southern and northern blots, for example, the detection reagents are hybridization probes followed by a fluorescent or chromogenic dye. In western blots, the detection reagents are antibodies followed by the use of conventional labeling techniques to detect the antibodies. Similar or analogous procedures, known among skilled biochemists, are performed with far western blots and eastern blots. Treatments such as these can also be applied directly to gels.

Additional examples of matrices with two-dimensional arrays of molecular species are mass spectroscopy targets. Still further examples are proteins, nucleic acids, or other biological species that have been deposited on a membrane or other support surface in regularly spaced or irregularly spaced two-dimensional arrays by such means as electrospraying, vacuum deposition, and pin spotting.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method of generating a corrected full image of a planar matrix supporting a two-dimensional analyte array, the method comprising:
  placing the planar matrix within 5 cm of a detector comprising one or more moveable solid-state image sensors, wherein a transparent faceplate is placed between the planar matrix and the detector, and wherein the transparent faceplate is deposited on or bonded directly to the solid-state image sensors;
  producing a dark signal pattern for the detector;
  positioning the image sensor(s) to two or more positions with respect to the planar matrix and acquiring with the image sensor(s) at the two or more positions a plurality of measurement patterns of electrical signals, wherein the electrical signals of the measurement patterns can be projected or otherwise made visible or detectable as sub-images of the planar matrix;
  measuring a plurality of temperatures at different locations along the image sensor(s);
  determining, using the plurality of measured temperatures, temperature variations among the different locations along the image sensor(s);
  adjusting the dark signal pattern according to the temperature variations among the different locations along the image sensor(s), wherein the adjusting comprises applying a function characterizing a variation of the dark signal pattern with temperature;
  subtracting the adjusted dark signal pattern from one or more of the plurality of measurement patterns; and
  subsequently assembling the sub-images into a full image of the planar matrix in accordance with the positions occupied by the image sensor(s) when the sub-images are acquired, wherein said assembling comprises stitching together at least two of the sub-images.

2. The method of claim 1, wherein the length, width, or both length and width of the planar matrix measure a minimum of about 3 cm.

3. The method of claim 1, wherein the solid state image sensor(s) are moved in discrete steps.

4. The method of claim 1, wherein the transparent faceplate is a fiber faceplate or a fiber taper.

5. The method of claim 1, wherein the transparent faceplate provides mechanical support to the analyte array.

6. The method of claim 1, wherein the maximum thickness of the transparent faceplate is about 10 mm.

7. The method of claim 1 further comprising:
  prior to the assembling of the sub-images into the full image, normalizing a first sub-image of the planar matrix and a second sub-image of the planar matrix, wherein the first and second sub-images each comprise two-dimensional arrays of pixels, wherein the first and second sub-images represent adjacent regions of the planar matrix, and wherein the first and second sub-images overlap at least one line of pixels.

8. The method of claim 1 further comprising:
  prior to the assembling of the sub-images into the full image, applying flat field correction within a sub-image of the planar matrix.

9. The method of claim 1 further comprising:
  prior to the assembling of the sub-images into the full image, applying flat field correction between two or more sub-images of the planar matrix.

10. The method of claim 1, wherein the transparent faceplate guides light from the planar matrix to the one or more solid-state image sensors.

11. The method of claim 4, wherein each of the one or more solid-state image sensors comprises a two-dimensional array of pixels, wherein the transparent faceplate comprises light pipes, and wherein each pixel receives light from a separate group of light pipes.

12. The method of claim 1, wherein the plurality of analytes emit chemiluminescent light.

13. The method of claim 1, further comprising:
  cooling the sensor array to reduce dark signal noise.

14. The method of claim 13, wherein a thermally insulating material is placed between the planar matrix and the sensor array.

15. The method of claim 13, wherein the cooling is stopped prior to the placing of the planar matrix within 5 cm of the detector.

16. The method of claim 1, wherein the solid-state image sensors are thin-film field effect transistors (TFT).

17. The method of claim 1, wherein the solid-state image sensors are complementary metal-oxide-semiconductors (CMOS).

18. The method of claim 1, wherein the solid-state image sensors are charge-coupled devices (CCD).

* * * * *